United States Patent
Bisaillon et al.

(10) Patent No.: US 8,888,498 B2
(45) Date of Patent: Nov. 18, 2014

(54) MULTILAYERED TISSUE PHANTOMS, FABRICATION METHODS, AND USE

(75) Inventors: Charles-Etienne Bisaillon, Montreal (CA); Guy Lamouche, Montreal (CA); Marc L. Dufour, Montreal (CA)

(73) Assignee: National Research Council of Canada, Ottawa, ON ( * ) Notice: Subject to any disclaimer, the term of this patent is extended or adjusted under 35 U.S.C. 154(b) by 912 days.

(21) Appl. No.: 12/792,073

(22) Filed: Jun. 2, 2010

(65) Prior Publication Data

US 2011/0062318 A1   Mar. 17, 2011

Related U.S. Application Data

(60) Provisional application No. 61/213,377, filed on Jun. 2, 2009.

(51) Int. Cl.
*G09B 23/30* (2006.01)
*G09B 23/28* (2006.01)
*A61B 5/00* (2006.01)

(52) U.S. Cl.
CPC ....... *G09B 23/285* (2013.01); *A61B 2560/0228* (2013.01); *A61B 5/00* (2013.01); *A61B 2560/0233* (2013.01)
USPC ........................................................ 434/267

(58) Field of Classification Search
CPC ....... G09B 23/28; G09B 23/285; G09B 23/30
USPC .................................................. 434/262, 267
See application file for complete search history.

(56) References Cited

U.S. PATENT DOCUMENTS

| | | | | |
|---|---|---|---|---|
| 4,481,001 A | * | 11/1984 | Graham et al. | 434/267 |
| 4,646,334 A | * | 2/1987 | Zerhouni | 378/18 |
| 4,870,666 A | * | 9/1989 | Lonn | 378/18 |
| 5,496,407 A | * | 3/1996 | McAleavey | 118/677 |
| 6,083,008 A | | 7/2000 | Yamada et al. | |
| 6,224,969 B1 | | 5/2001 | Steenbergen et al. | |
| 6,315,447 B1 | * | 11/2001 | Nord et al. | 378/207 |
| 6,675,035 B1 | | 1/2004 | Grable et al. | |
| 6,807,876 B2 | | 10/2004 | Beck et al. | |
| 7,059,168 B2 | * | 6/2006 | Hibi et al. | 73/1.86 |
| 7,288,759 B2 | * | 10/2007 | Frangioni et al. | 250/252.1 |

(Continued)

OTHER PUBLICATIONS

Bays et al., "Three-Dimensional Optical Phantom and it's Application in Photodynamic Therapy", Lasers in Surgery and Medicine, 1997, 21(3), p. 227-234.

(Continued)

*Primary Examiner* — Gene Kim
*Assistant Examiner* — Alyssa Hylinski
(74) *Attorney, Agent, or Firm* — Catherine Lemay

(57) ABSTRACT

A method for producing a multilayer tissue phantom involves successively forming at least two layers, each layer formed by depositing a viscous flowable material over a supporting element or over a previously formed layer of the phantom supported by the supporting element, selectively redistributing the material while material is solidifying to control a thickness distribution of the layer, and allowing the material to solidify sufficiently to apply a next layer. The supporting element supports the material in 2 or 3 directions and effectively molds a lumen of the tissue. The neighboring layers are of different composition and of chosen thickness to provide desired optical properties and mechanical properties of the phantom. The phantom may have selected attenuation and backscattering properties to mimic tissues for optical coherence tomography imaging.

13 Claims, 7 Drawing Sheets

(56) References Cited

U.S. PATENT DOCUMENTS

| | | | |
|---|---|---|---|
| 7,419,376 B2 | 9/2008 | Sarvazyan et al. | |
| 7,439,493 B2* | 10/2008 | Teppaz et al. | 250/252.1 |
| 7,748,971 B2* | 7/2010 | Hochsmann et al. | 425/90 |
| 8,057,236 B2* | 11/2011 | Miau et al. | 434/267 |
| 2002/0170339 A1* | 11/2002 | Passi et al. | 73/1.86 |
| 2004/0076258 A1* | 4/2004 | Zyromski | 378/16 |
| 2005/0123178 A1* | 6/2005 | Teppaz et al. | 382/128 |
| 2006/0105102 A1* | 5/2006 | Hochsmann et al. | 427/180 |

OTHER PUBLICATIONS

Beck et al., "Design and Characterisation of a Tissue Phantom System for Optical Diagnostics", Lasers in Medical Science, 1998, 13(3), p. 160-171.

Bisaillon et al,. "Deformable and durable phantoms with controlled density of scatters", Physics in Medicine and Biology, 2008, 53(13), p. N237-N247.

Lualdi et al., "A Phantom with Tissue-Like Optical Properties in the Visible and Near Infrared for Use in Photomedicine", Lasers in Surgery and Medicine, 2001, 28, p. 237-243.

Oldenburg et al., "Imaging magnetically labeled cells with magnetomotive optical coherence tomography", Optics Letters, 2005, 30(7), p. 747-749.

Pogue et al., "Review of tissue simulating phantoms for optical spectroscopy, imaging and dosimetry", Journal of Biomedical Optics, 2006, 11(4), p. 041102-0-041102-16.

Urso et al., "Skin and cutaneous melanocytic lesion simulation in biomedical optics with multilayered phantoms", Physics in Medicine and biology, 2007, 52(10), p. N229-N239.

Beck et al., "Design and Characterization of a Tissue Phantom System for Optical Diagnostics", Lasers in Medical Science, 1998, 13(3), p. 160-171.

Bisaillon et al., "Deformable and Durable Phantoms with Controlled Density of Scatters", Physics in Medicine and Biology, 2008, 53(13), p. N237-247.

* cited by examiner

MULTILAYERED TISSUE PHANTOMS, FABRICATION METHODS, AND USE

This application claims the benefit of U.S. Provisional Patent Application Ser. No. 61/213,377 filed Jun. 2, 2009, the entire contents of which are herein incorporated by reference.

FIELD OF THE INVENTION

The present invention relates in general to phantoms for biomedical applications, their fabrication and their use, more specifically, the invention relates to phantoms targeting endoscopic applications of biomedical optics, including optical techniques that characterize the detailed structure of tissues as a function of depth.

BACKGROUND OF THE INVENTION

An optical phantom is a fabricated sample that provides an optical response similar to biological tissues for examination by one or more optical imaging system. In many cases, the interaction of electromagnetic (EM) radiation (herein "light") with a tissue is described by the scattering and the absorption processes. In a scattering process, light is essentially redirected in a different direction. In the absorption process, light is absorbed and energy is converted into a different form. Therefore, phantoms are often made of scattering and/or absorbing materials or mixtures that can produce the desired response. In the literature, one can find a variety of phantom fabrication processes with different materials that provide optical responses somewhat similar to tissues. The main differences between the resulting phantoms are often in terms of other important properties, like mechanical properties or durability.

Many phantom compositions are made of liquid or gel. These phantoms suffer from a conservation period limited to months in the best cases due to perishing or water evaporation (U.S. Pat. No. 7,288,759 to Frangioni et al.). A housing is sometimes used to increase durability but can be inconvenient in use because such housings are known to influence measurements (U.S. Pat. No. 6,675,035 to Grable et al.).

Phantoms that are durable for years can be obtained with polymeric matrices such as polyester, epoxy resins or dried poly(vinyl alcohol) mixed with inorganic components (U.S. Pat. No. 6,083,008 to Yamada et al., and U.S. Pat. No. 6,224,969 to Steenbergen). However, these matrices are hard and do not provide mechanical properties similar to soft tissues. This limits some uses of phantoms, for example in training surgeons on operations, as haptic and tactile responses are not similar, especially for procedures like endoscopy.

Phantoms with elastomeric matrices, like silicone, combine durability with mechanical properties somewhat similar to soft tissues. These were presented in a number of publications reviewed by Pogue and Patterson, in Journal of Biomedial Optics, 11 (4), 041102, (2006). The mechanical properties can also be adjusted by modifying the silicone formulation (Oldenburg et al. in Optic Letters, 30 (7), 747, (2005) and U.S. Pat. No. 7,419,376 to Sarvazyan). Some optical properties can be obtained by introducing inorganic powders in the silicone matrix. An experimental calibration can be conducted to relate the powder concentrations and the optical properties, like by Beck et al. in Lasers in Medical Science, 13 (3), 160 (1998) and by Lualdi et al. in Lasers in Surgery and Medicine, 28, 237, (2001). Some slab shape phantoms using different mixtures representing multiple skin layers and lesions have also been published, for example by Urso et al, in Physics in Medicine and Biology, 52 (10), N229, (2007).

Very few phantoms have been designed for endoscopic applications. Endoscopic optical applications are increasing with the development of specialized optical probes that are able to deliver light to internal organs using optical fibers. Many of these organs, like blood vessels, bronchi, the esophagus, the colon, etc. have openings of somewhat cylindrical or tubular geometries, or define somewhat closed cavities. Herein a lumen is used to refer to a tubular or a closed cavity that is formed of walls on two or three sides. Such walls generally include tissues built up in layers, each of which having different composition, function, and optical and mechanical properties.

Silicone-based phantoms with complex geometries have been molded in various shapes (U.S. Pat. No. 6,807,876 and Bays et al. in Lasers in Surgery and Medicine, 21(3), 227, (1997)) but do not show a detailed layered structure. A molding process limits the shapes and the dimensions of the phantoms to the ones of the available molds. Furthermore molding of very thin layers, less than about 25 µm for example, can be exceedingly difficult, generally requires high pressure (which can damage other delicately formed features) and is prone to failure.

Further still, it is generally desired to provide phantoms that contain inclusions such as features that optically and/or mechanically represent lesions, tumors, scar tissues, inclusions, herniations etc. While highly planar features can be readily provided, even between layers of a phantom, by application of paint or powder prior to a subsequent overmolding step, the embedding of solid objects within a mold can be exceedingly difficult. A general failure to provide precise localization of the object within a mold and numerous defects are recurring problems with solid objects in molds. These problems may be exacerbated by subsequent overmolding steps.

Finally it is very difficult to produce very uniform thickness layers, or to provide a very high measure of control of thickness as a function of position of the layer, unless the phantom is molded. With multilayered structures, the costs and tolerances of many molds that fit inside one-another is prohibitive for many applications.

There remains a need for multilayer optical phantoms representing animal tissues and organs containing lumens, and for methods of fabricating same, especially for fabrication methods that permit precise control of the layer thicknesses, down to layers of the order of 10 µm, and permitting solid body inclusions between the layers.

BRIEF SUMMARY OF THE INVENTION

In accordance with the present invention a method is provided for fabrication of tissue-like phantoms that represent animal tissues and organs containing lumens, with tissue details like multiple layers. Each layer of the phantom has independently controlled optical properties that mimic the optical/infrared response of the targeted tissue layers. The layers may have controlled mechanical properties to mimic the behavior of the tissue. The first layer of a phantom is created by the application of the layer material on a supporting element, which effectively forms the lumen of the phantom. Subsequent layers are formed on top of previous layers, generally while the first layer is supported by the supporting element. The forming of the layer involves depositing a viscous flowable material and, before it completely solidifies, selectively redistributing the material to control a thickness distribution of the layer. A desired thickness distribution of the layer is preferably obtained by relative rotational motion between the supporting element and a wiper which contacts the material. The wiper may substantially remove material (e.g. if it is sharp and meets the material at a steep angle), or may substantially only spread the material (e.g. if it is dull or meets the material at a shallow angle), and may both spread and remove material at any given point in time.

The supporting element can be any structure that will form the lumen in a desired shape. It can be, but is not limited to, a shaft, a rod, a mandrel or an inflated balloon that could be deflated for removal. The shape of the supporting element is not restricted to one with rotational or translational symmetry, but is preferably defined with respect to a single axis of rotation.

It is an aspect of the invention to be able to adjust the optical properties of the phantom layers. Different optical properties are obtained with different concentrations of one or more powders that scatter and/or absorb light, in a polymer matrix. Control is obtained by establishing a relationship between the concentrations of said products and the optical properties of the phantoms or the signal they produce when measured with a certain system. Such a relation can be wavelength dependent. In a preferred embodiment, highly stable inorganic powders and pigments are used as the products that scatter and/or absorb light to ensure high durability. The preferred inorganic powders and pigments are aluminum oxide ($Al_2O_3$), titanium oxide ($TiO_2$), and carbon black.

It is another aspect of the invention to be able to control the mechanical properties of the phantom layers while approaching those of tissue. This is particularly useful in providing lifelike response to endoscopic probing, stent deployment, balloon dialation, and numerous other procedures within lumens of animals, which require significant training, as they must be performed without any cues other than tactile, and those provided by imaging.

Therefore, in many cases, the possible materials for the phantoms are elastic materials. In a preferred embodiment, the chosen elastic materials are also highly stable, so that their properties vary minimally in time. Such materials include silicones and thermoplastics that have mechanical properties that depend on the polymer formulation and possibly also on polymerization conditions.

In certain embodiments, the phantoms can also have other solid structures integrated to mimic pathologies, etc. The structures can be added during or after the process of the layer formation. They can be internal or external to the layers. The structures can be solid, liquid or gaseous. In the case of a liquid or gas, a void can be created by first adding a temporary material, crafting the phantom, removing the temporary material, and then filling the void with the desired product. In addition, phantoms can be attached (welded, glued, fused, stitched, etc.) together to create more complex structures.

The invention provides various ways of using the phantoms. The phantoms can be used to calibrate a system. A calibration procedure consists in measuring the phantom with a specific system, and then quantifying the performances, for example using previously ascertained properties of the phantom. The measurements can also be compared with images of the phantom taken with different imaging systems. Qualitative or quantitative differences between the images may be used to evaluate, compare or test the imaging systems.

Another way to use the phantoms is to use them as a convenient and cost-effective replacement of real tissue for the training of medical staff on the use of imaging systems. A collection of phantoms that mimic a variety of tissue conditions, including normal tissues and pathological tissues, may have further value for such training or for the evaluation of imaging systems.

The phantom may be integrated in a setup that recreates realistic conditions such as contact with circulating fluids, with a range of temperatures or pulsating pressure. The phantoms preserve their properties after having been exposed to measurements in realistic conditions. For example, a blood vessel phantom will maintain its integrity after being exposed to a liquid such as saline solution or blood, either static or in circulation, either with pulsating pressure for simulating heart beats or not. That property is useful because it can be used to quantify the performances of different instruments operating under realistic conditions and then to compare those performances.

It would then be possible to test medical procedures. The medical procedure can be a normal procedure such as the deployment of a stent or a balloon angioplasty; it can also be a new medical procedure, tool, or implant that is being developed or improved.

Phantoms fabricated using our method can be used as a reference standard. With some materials such as alumina and carbon black in silicone the phantoms retain their optical and mechanical properties over a very long period. They can therefore be used to evaluate and quantify the optical performance of an instrument over time. The results of those evaluations can be compared for a given instrument, at different times to ensure that there is no degradation and quantify any differences. It is of strategic importance for a medical team to be able to verify the performance of an instrument before its use in an operating room.

The phantoms, having some known or selected optical and mechanical properties can be reproduced with substantially the same properties. Such a phantom, available in multiple, substantially identical copies, can be distributed to various users, (medical teams, commercial users, research teams or to other users) and serve as a reference standard. Such a reference can then be compared, with different real tissue conditions (normal, abnormal but healthy, or pathological).

Our phantom can be used as a replacement for real tissue for the development or testing of various procedures. The procedure may be a medical procedure such as the deployment of a stent, angioplasty, a blood flushing technique, like removal of plaque from a lumen, or another procedure where the measurement of the condition of the tissue may be involved.

For example, an OCT device operated at a typical wavelength of 1300 nm can not see through blood. The blood is therefore displaced temporarily and generally replaced by a liquid transparent at 1300 nm such as a saline solution. The liquid may be inside a compliant balloon and the probe is used inside the balloon that must be inflated to the dimension of the artery. Another approach consists in injecting the saline solution directly into the artery. If the volume is large enough, over a short period of time the blood would be almost entirely replaced by the saline. The OCT probe can be used efficiently during a few seconds. The flushing procedure may be initially developed using a phantom. The OCT probe would be used to quantify the effectiveness of the method.

Optical measurements within an artery are often complicated by the geometrical deformation, like diameter size fluctuations, that are caused by blood pressure changes. Our phantom has mechanical properties that mimic the mechanical properties of a vessel. Therefore, it is possible to reproduce the geometrical deformations caused by the heart beats. Using that realistic model, it becomes easier to develop robust algorithms that would be able to recognize the target features even in the presence of heart beats and like factors that complicate measurements in living tissues.

The phantoms may mimic mechanical properties of tissue structures sufficiently to permit surgeons to learn how to operate on the tissues with the phantoms. Concurrently the phantoms can be used with new or old tools, devices, implants etc. and can teach the user how to use the same, with or without the functions of the imaging system. A surgeon may train on the phantom to use an imaging device and 3D volume visualization software to find pathological features, like obstructing plaques in arteries. Phantoms can be produced, stored, and disposed of, far more effectively and at less expense than an animal, or human cadaver tissues, especially given ethical considerations. Additionally necrotic tissue has properties that are difficult or expensive to reproduce in order to mimic living tissue. Abnormal tissues that are not very common can be reproduced using phantoms, once characterized making it easier to train someone to identify a larger set of possible tissue conditions.

In a specific embodiment, the phantoms represent blood vessels. Blood vessels typically have three distinct layers, the intima, the media, and the adventitia. Each of these layers can be affected by diseases like atherosclerosis, which can take several forms. The choice among available materials to mimic the optical and mechanical properties of the layers and diseases permits high durability, in the range of years. The present invention includes the fabrication of blood vessel phantoms with morphological details representing the tissue layers and various forms of blood vessel diseases. As the intima is typically less than 25 µm thick, molding such phantoms is impractical.

Specifically, in accordance with the invention there is provided:
A method for producing a multilayer tissue phantom, the method comprising:
  successively forming at least two layers, each layer formed by:
    depositing a viscous flowable material to encircle at least a portion of a supporting element or over a previously formed layer of the phantom supported by the supporting element;
    selectively redistributing the material while material is solidifying to control a thickness distribution of the layer; and
    allowing the material to solidify sufficiently to apply a next layer,
  wherein at least neighbouring layers are of different composition, and
  wherein the compositions and thickness distributions of the layers are chosen to provide desired optical properties and mechanical properties of the phantom.
The above method wherein selectively redistributing the material comprises contacting the material with a wiper while the wiper is in relative rotational motion with respect to the material.
The above method further comprising successively forming a third layer.
The above method wherein selectively redistributing:
  is performed by the wiper that extends a length of the phantom and bears a desired profile across that length whereby different thicknesses of the deposited layers may be deposited relative to the previously deposed layer, or the supporting surface;
  is performed by the wiper, which extends a fraction of the length of the phantom, the wiper moving axially across the length of the phantom during the relative rotational motion, wherein radial motion of the wiper imparts a desired profile to the layer;
  is performed in part by contacting the material with a wiper while rotating the supporting element along an axis wherein control over a radial position of the wiper is faster than the relative rotational motion and the layer has different thicknesses at different angles; or
  is performed by the wiper which consists of a blade, an edge, a sharp point, or a rubber wiper.
The above method wherein the viscous flowable material deposited:
  comprises a polymer resin selected for durability;
  comprises at least 40 wt. % molten polymer resin;
  comprises at least 40 wt. % curable polymer resin;
  comprises at least 40 wt. % dissolved polymer in a volatile solvent;
  comprises a silicone;
  comprises a silicone with a poly(dimethyl siloxane);
  comprises, for each layer, a proportion of resin of silicone to poly(dimethyl siloxane) chosen to obtain a desired mechanical property for the layer.
  comprises a same polymer resin in the composition of all layers;
  comprises a selected amount of 0.0001-100 mg/ml of an optical attenuating additive;
  comprises a selected amount of 0.0001-100 mg/ml of an optical scattering additive;
  comprises an amount of an optical scattering and optical attenuating powder additives selected to provide:
    a backscattering amplitude for the layer proportional to a square root of a sum of the squared backscattering amplitudes of each of the powder additives for given concentrations; and
    an attenuation coefficient for the layer equal to a sum of attenuation coefficients of each of the powder additives for given concentrations;
  comprises a selected amount of 0.0001-100 mg/ml of at least one of the following: carbon black, titania, and alumina, in powdered form;
  comprises a selected amount of 0.0001-100 mg/ml of carbon black; or
  comprises a selected amount of 0.0001-100 mg/ml of alumina.
The above method wherein throughout the forming, the phantom is supported by the support element, which:
  consists of a shaft, a rod, a tapered mandrel, or an inflated balloon;
  is substantially covered by the phantom in 2 dimensions;
  is substantially covered by the phantom in 3 dimensions;
  has a profile corresponding to a cavity within an organ of an animal;
The above method wherein depositing the viscous flowable material comprises:
  applying the material through a conduit that is translated axially over a length of the phantom said supporting element or the said previous layer;
  applying the material through a conduit connected to the wiper;
  applying the material through a conduit that is positioned with respect to an axis of the relative rotational motion that is at a substantially fixed angle with respect to the wiper;
  applying the material at a part of a surface of the support element or the previously formed layer, and allowing a viscous flow under gravity to at least substantially coat the surface;

applying the material at a part of the surface that is rotating at a rate that is fast enough to prevent the material from dripping under the force of gravity, and slow enough to prevent ejection of the material by centrifugal force; or concurrently applying the material at one location while contacting previously deposited material at another location to selectively redistribute the material.

The above method wherein allowing the material to solidify to a desired degree comprises controlling a temperature distribution of the layer and selecting a composition of the material that solidifies at a temperature higher than an ambient temperature.

The above method:
- wherein forming one of the layers further comprises embedding a feature at a location on the outer layer after the selective redistributing;
- wherein forming one of the layers further comprises embedding a solid feature at a location on the outer layer after the selective redistributing;
- wherein forming one of the layers further comprises applying a compound at a location on the outer layer after the selective redistributing;
- wherein forming one of the layers further comprises spraying a compound at a location on the outer layer after the selective redistributing;
- wherein forming one of the layers further comprises embedding a solid feature at a location on the outer layer after the selective redistributing, and
- further comprising, after one or more subsequent layers are formed, penetrating the one or more subsequent layers to inject or remove material in contact with the solid feature;
- wherein forming one of the layers further comprises embedding a solid feature at a location on the outer layer after the selective redistributing, and further comprising after one or more subsequent layers are formed, penetrating the one or more subsequent layers to inject a fluid to dissolve the solid feature, followed by removing the fluid and solute;
- wherein forming one of the layers further comprises embedding a solid feature at a location on the outer layer after the selective redistributing, and further comprising after one or more subsequent layers are formed, penetrating the one or more subsequent layers to inject a fluid to dissolve the solid feature, followed by removing the fluid and solute and refilling a pocket formed within the phantom with another material;
- wherein forming one of the layers further comprises embedding a solid feature at a location on the outer layer after the selective redistributing, and further comprising after one or more subsequent layers are formed, locally heating the solid feature until it exceeds a critical temperature, and penetrating the one or more subsequent layers to remove a fluidized part of the solid feature;
- wherein forming one of the layers further comprises embedding a solid feature at a location on the outer layer after the selective redistributing, and further comprising after one or more subsequent layers are formed, locally heating the solid feature until it exceeds a critical temperature, penetrating the one or more subsequent layers to remove a fluidized part of the solid feature, and refilling a void created by the removal of the fluidized part with another material;
- wherein forming one of the layers further comprises embedding a solid feature at a location on the outer layer after the selective redistributing, and further comprising after one or more subsequent layers are formed, locally heating the solid feature until it exceeds a critical temperature, penetrating the one or more subsequent layers to remove a fluidized part of the solid feature, refilling a void created by the removal of the fluidized part with another material, and repairing a hole in the phantom produced by the penetration;
- wherein forming one of the layers further comprises embedding a solid feature at a location on the outer layer after the selective redistributing, and further comprising after one or more subsequent layers are formed, locally heating the solid feature until it exceeds a critical temperature, penetrating the one or more subsequent layers to remove a fluidized part of the solid feature, and refilling a pocket formed within the phantom with a fluid;
- wherein forming one of the layers further comprises embedding a solid feature at a location on the outer layer after the selective redistributing, and further comprising after one or more subsequent layers are formed, locally heating the solid feature until it exceeds a critical temperature, penetrating the one or more subsequent layers to remove a fluidized part of the solid feature, refilling a pocket formed within the phantom with a fluid, and repairing a hole in the phantom produced by the penetration;
- further comprising applying a non-covering material in a liquid form on one of a part of an inner surface of an inner layer and a part of an outer surface of an outer layer and directing a flow of the non-covering material under the action of gravity to cover the part of the inner or outer surface without covering the whole of the inner or outer surface;
- further comprising applying a non-covering material in a liquid form on one of a part of an inner surface of an inner layer and a part of an outer surface of an outer layer and directing a flow of the non-covering material under the action of gravity to cover the part of the inner or outer surface without covering the whole of the inner or outer surface, the non-covering material having a same composition as the inner layer or outer layer; or
- further comprising producing a hole in one of a part of an inner surface of an inner layer and a part of an outer surface of an outer layer and depositing a non-covering material in a liquid form in the hole, the non-covering material being of different composition than the inner or outer layer.

A collection of phantoms obtained by applications of the above method to serve as standard samples representative of a single tissue in abnormal healthy, normal healthy and/or pathological states.

A use of a phantom produced according to the above method comprising inserting the phantom into the optical imaging system and imaging a portion of the phantom.

The above use further comprising:
- placing the phantom in contact with other tissue-like structures or liquids;
- submitting the phantom to temperature variations or pressure variations that can be found normally or exceptionally in an animal;
- testing a tool, process or implant on the phantom;
- attaching a second phantom fabricated according to the method of claim 1 to the phantom such that lumens are coupled The above use further comprising comparing independently characterized parameters of phantom to calibrate the system.

The above use further comprising inserting the phantom into a second optical imaging system, imaging the phantom using the second system, and comparing the image data from the system and second system to compare the two.

The above use further comprising operating the system in a training mode to provide the user with feedback on the operation of the system.

A phantom consisting of a chamber covered by a structure having at least 2 polymer-based layers having different compositions exhibiting different scattering and attenuation values within optical and infrared regions of the electromagnetic spectrum wherein one of the at least two polymer-based layers has a thickness of less than 25 µm. and A phantom consisting of a chamber covered by a structure having at least 2 polymer-based layers having different compositions exhibiting different scattering and attenuation values within optical and infrared regions of the electromagnetic spectrum wherein a solid object is embedded.

The above and other features of the present invention will become apparent in the following description. However, it is to be understood that the scope of the invention is not limited to the specific embodiment described in this document.

BRIEF DESCRIPTION OF THE DRAWINGS

In order that the invention may be more clearly understood, embodiments thereof will now be described in detail by way of example, with reference to the accompanying drawings, in which.

DETAILED DESCRIPTION OF THE INVENTION

Figure 1:
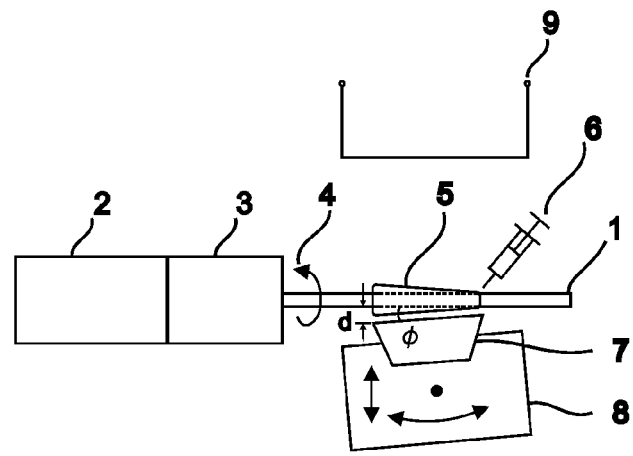
FIG. 1 schematically illustrates a setup used in the formation of a layer of a phantom in accordance with a first embodiment of the invention in which a wiper is used that covers an extent of the phantom.
Figure 2:
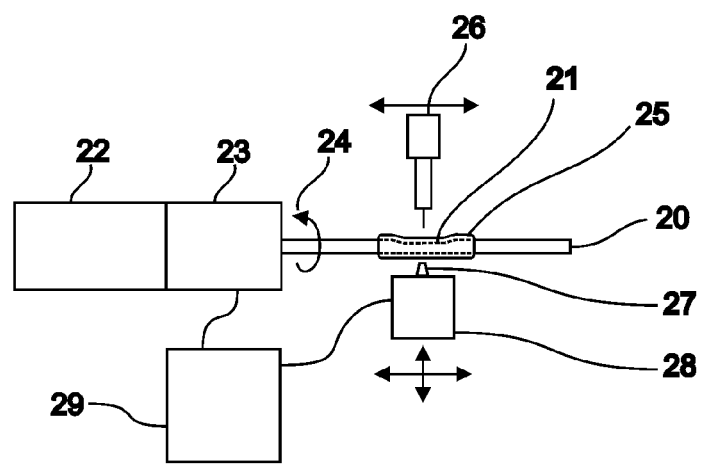
FIG. 2 schematically illustrates a setup used in the formation of a layer of a phantom in accordance with a second embodiment of the invention in which a wiper is used and is translated axially to cover an extent of the phantom.

The invention provides a fabrication method and uses for phantoms that mimic the optical response and/or the mechanical behavior of tissue structures that at least partially enclose lumina within walls having multiple tissue layers. One aspect of the method involves a controlled process for fabricating layers of a specified geometry when one or more of the layers is/are thin, or contain(s) embedded solid objects. Applicant further provides a method for controlling an optical response of the phantom layers to match the response of the tissue structure. Applicant further provides a method to fabricate phantoms that have mechanical response similar to those of actual tissues.

Layer Fabrication

A process for fabricating a multi-layer structure of a desired geometry involves forming successive layers of the phantom. Herein a layer is taken to be a macroscopically homogeneous composition (although exogenous features may be attached or embedded in separate steps, and microscopic inclusions may not be uniformly enough distributed to be homogeneous at some scales, and may vary somewhat in density such as in graded deposition) that is substantially continuous around the lumen of the phantom, throughout at least 50% of a transverse length of the phantom. Herein the "lumen" is a volume of an internal passage surrounded by a tissue structure (or the phantom which mimics the same).

The layer formation process involves the deposition, redistribution and solidification of material that is initially in a viscous liquid state. Throughout this forming, the deposed layer is supported by a supporting element. The supporting element defines the shape the lumen of the tissue structure modeled by the phantom. It can be in the shape of a shaft, a rod, a mandrel, or an inflated balloon, and may or may not be rotationally, axially, or otherwise symmetric. The supporting element may be designed to receive the material only along a fraction of its length, and this fraction may include an end (in which case the lumen is a chamber closed at one end), or not (in which case the lumen is tubular). The supporting element may have a generally cylindrical shape, but doesn't necessarily have the radial or the longitudinal regularity of an exact cylinder.

The deposition may be performed by pushing the viscous liquid material through a conduit held over the supporting element, although in alternate embodiments the material may be poured, dipped, or sprayed onto the supporting element (or phantom thus far produced). This may be performed manually, or by pushing the material through a number of holes spaced axially along the supporting element, by a scanning arm that moves the conduit axially across the supporting element, or manually, for example, through a syringe. The supporting element may be rotating during the supply of the material, or only after the supply of the material is complete, depending on a viscosity of the liquid material, a solidification rate of the material, and a desired thickness of the layer. It is usually preferable for the material to remain in a viscous liquid state until at least the material is spread all around the supporting element (or the previously deposited layer supported thereon) so that a seam is not formed of solidified material, resulting in a weaker joint and non-uniform material properties.

Furthermore, the material may be supplied while a wiper (or other shaping element) redistributes the material deposited, or may be applied before wiping commences. If a wiper used extends the length of the phantom, and the supply of the liquid operates over the entire length, an angular offset (relative to the axis) between the wiper and the number of holes to provide a desired dwell time between when the material is applied to a surface (of the supporting element or the previously deposited layer) before the wiper is encountered. Similarly if the conduit applied the material from a point and a relatively narrow wiper is used to shape the deposited material, they may be scanned together while the supporting element is in rotation, and a fixed axial and/or angular offset between the wiper and supporting element may be chosen to provide the desired dwell time. Applicant has continuously rotated the supporting element during the forming which includes deposition, redistribution, and solidification phases. The deposition of the layer may continue with the same material being deposited over the same material to produce a layer that is thicker than can be applied without dripping and wastage to produce a monolithic material layer, and a wiper may be only applied sparingly throughout the majority of the deposition, as will be appreciated.

An element, located in the vicinity of the supporting element, shapes the layer by removing excess liquid material, preferably before the complete solidification. To ensure control of a thickness distribution all around the tubular structure for each layer, the supporting element and the shaping element (preferably a wiper) are in relative rotational motion. It is also possible to have the supporting and the shaping element in relative translational motion synchronized with the rotation to obtain uneven but controlled thickness at any point. Multiple layers are obtained by successive deposition and solidification of viscous liquid material of different compositions leading to different optical and/or mechanical properties. For each layer, the distance between the supporting element and shaping element is adjusted to obtain the desired thickness. It is also possible to use external means for precisely monitoring the layer thickness during the action of the shaping element, and further properties may be monitored throughout deposition.

To create a new layer, the material that is deposited is replaced by a material of a different composition. Enough time, and thermal conditions are provided to solidify the previously applied material to enable the present surface of the phantom to support the application of a new layer. The different composition may be a blend of the same components in different proportions, or different compounds. The compounds envisaged are principally thermoplastics and elastomers, but may contain various additives, including those that alter the optical properties of the material, such as colour, absorption (at given frequencies), and scattering. Advantageously by changing concentrations of some formulations, different mechanical properties (e.g. Young's modulus) can be changed, while providing excellent bonding of adjacent layers. It will be appreciated that certain graduated properties can be provided within a same nominal layer by continuously varying a density of an additive during the coating.

FIG. 1 is a schematic illustration of an apparatus in accordance with an embodiment of the present invention. The apparatus consists of a supporting element shown as a cylindrical shaft 1. The shaft 1 is coupled to a motor 2 through a reducer 3 to rotate at a controlled speed. The circular arrow 4 indicates a direction of rotation of the shaft around its longitudinal axis. The preferred rotation speed is of the order of one rotation per second for usual viscosities and temperatures of the materials used, but in any case should be maintained within a certain range. The lower limit of the range is somewhat higher than a speed where the viscous liquid would fall by gravity and drip. The higher limit of the range is somewhat lower than a speed where the viscous liquid would be ejected by centrifugal force. At a balanced speed the action of gravity is counterbalanced by a flow rate of the material permitting continuous, even coating of the material to build up.

The viscous liquid material 5 is deposited by manually translating a syringe 6 along the shaft axis while the shaft 1 is rotating and is substantially concurrently shaped by a knife blade 7. The blade 7 has a square profile that extends the length of the phantom and is suited to create a layer with a cylindrical or a conic outer surface, regardless of the shape of the previous layer. Naturally the blade 7 can be switched with one having a variety of profiles.

The blade 7 is mounted on a support 8 that allows the precise adjustment of the distance (d) and the angular position between the blade and the shaft. The distance from the axis to the blade 7 in the illustrated embodiment is provided by rotational movement of the blade 7 relative to the axis, although it could equally be provided by other motion having a radial component, such as tangential motion. The blade 7 is in a horizontal plane that passes through the axis. The angle ($\phi$) created by the blade 7 and the axis in the horizontal plane can be adjusted.

A heating element 9 may be located in the vicinity of the shaft 1, particularly if the material has accelerated solidification at higher temperature. The blade's position d can be changed, in a controlled manner as layer material is deposited or between successive depositions, either manually, as shown, or using automated equipment known in the art. A different syringe can be used for the new material. Initial viscosity of the liquid polymer and cure temperature, which impacts on the time of curing, can both be used to control, to some extent, the spreading of the liquid mixture. This allows limited control on the shape of the layer. Applicant has found that excellent control of thicknesses at every point can be provided with the use of a wiper.

FIG. 2 schematically illustrates a second embodiment of the invention that incorporates axial translation of a smaller shaping element to produce a desired layer profile with a radial component of motion. This allows controlling the thickness of a layer at every location on the surface of the phantom, meaning all axial positions along the phantom, and all positions around the phantom, if the radial motion is faster than the cycle rate of the rotation. The principal differences between the embodiment of FIG. 2 with that of FIG. 1 is the inclusion of a scanning dispenser, and machining of the shaft 20, both of which are considered to be well within the scope of one skilled in the art to produce.

The supporting element is a cylindrical shaft 20 that is machined with a flat groove 21 to obtain a d-shape on a short section of the shaft 20. The shaft 20 is coupled to a motor 22 through a reducer 23 to rotate at a controlled speed, as in the embodiment of FIG. 1. Arrow 24 indicates a direction of rotation of the shaft around its longitudinal axis. Viscous liquid material 25 is deposited through a conduit 26 in translation along the axis. The flow of material through the conduit 26 does not entrain air bubbles or cause splattering or spraying, and ranges from 0.01-50 ml/min. The conduit is controlled to release the material 25 (via a pump and a viscous liquid mixing chamber well known in the art and not shown) at a desired rate that can be varied during translation to assist in the shaping of the layer. The material 25 is shaped by a narrow rubber wiper 27. The wiper 27 is mounted on a biaxial translation stage 28. The biaxial translation stage 28 is connected to a programmable controller 29 that receives a signal for synchronization with the rotational motion. The programmable controller 29 allows the rubber wiper to follow any desired pattern that determinates the layer thickness at all locations. Programmable controller 29 may further control the release of material by volume and the axial motion of the conduit 26. While the translation of the conduit 26 along the axis is shown schematically as separate from the wiper, it will be appreciated that there may be a single stage for moving both the conduit 26 and the wiper 27, which may have a fixed, configurable offset from each other in the axial and/or radial (relative to the axis) directions as desirable for the material 25 to be in a desired condition upon encountering the wiper.

At a change in layer, different material will be deposited through the conduit 26, or through a different conduit. If a same conduit 26 is used for depositing different layers the process may involve switching supplies, evacuating the supply conduit 26 and purging the supply conduit 26 as well known in the art. The subsequent material may be mixed in a same hopper that was previously used with the addition of material to change relative concentrations of components, in which case the conduit 26 may simply be purged.

It is well known how to produce a variety of materials for use in the present invention. Numerous methods of producing a viscous fluid that is polymerizable, settable, gelable, curable or vitrifiable under chosen thermodynamic conditions are fully applicable. The process may involve melting a resin that will cure under controlled thermal conditions, or dissolving the polymer in a volatile solvent that evaporates to form the polymer. Evaporation may be expedited by vacuum or forced air.

The material may be prepared in a conventional manner by weighing the needed amounts of additives for producing desired properties of the layer, selecting mechanical properties for the layer by selecting a formulation for the polymer matrix, and then adding the necessary volume of the selected resin in with the additives. In some cases, a viscosity of the material can be decreased with the addition of a thinner in a suitable volume. The mixture preferably undergoes extended mixing, to homogenize the material. Afterwards, if needed, the thinner may be evaporated in vacuum for a few hours. Finally a reactive may be added and dispersed by manual mixing prior to deposition through the conduit.

The choice of product and composition of the polymer matrix mostly impacts on the mechanical properties of the phantoms, which is discussed further, as there are a wide variety of polymers that are substantially transparent and can retain the additives.

Optical Properties

Applicant has used the following methods to produce layers that have optical properties similar to those of tissue layers. Dyes may be added to match chromatic response of the tissues. These may be omitted if the phantom is going to be imaged only with narrowband light. The materials used in layer fabrication may principally mimic the optical response of a tissue layer as detected with a specific optical characterization or imaging technique. In order for a phantom to mimic the tissue response, not all optical properties need to be reproduced.

In some cases, off-the-shelf materials having optical properties close to the target tissue may be used. In order to gain better control on the optical properties of the phantoms, one can mix materials in concentrations selected according to known relationships. The relationship can be obtained either theoretically, using the material parameters and a model of the system, or experimentally by fabricating sets of samples with different concentrations and measuring the response of the system. Such a technique therefore allows mimicking tissues exhibiting a wide range of optical properties.

In one embodiment of current interest, phantoms are fabricated to mimic the response of tissues to optical coherence tomography (OCT) systems. To mimic an OCT response, a phantom must provide backscattering, attenuation, and a speckle structure. An OCT system collects a portion of the light that is backscattered along the depth of the tissue. In a phantom, scattering materials provide backscattering. The amplitude of backscattering decreases with depth from attenuation due to scattering, including backscattering, and due to absorption. This backscattering and attenuation can be mimicked by adding various materials that scatter and/or absorb light into the polymer matrix Optical properties of tissues constituents are wavelength dependent. Therefore, in general, as is cost effective, a phantom will be designed to mimic a tissue over a limited wavelength range. In a tissue, a dense assembly of structures (nuclei, mitochondria, cell membrane, etc) scatters light, and since OCT is a coherent imaging technique, resulting images contain speckle. In a phantom, this speckle can be obtained by using a dense assembly of scatterers the size of which being on the order of or smaller than the wavelength of the OCT imaging.

Optical backscattering and attenuation needs to be mimicked only on a length scale larger than the speckle size. For each layer of a given tissue, OCT measurements are averaged over many speckles to provide target values for backscattering and attenuation. Consequently, to obtain optical properties for a tissue layer or a phantom layer, the OCT signal is averaged for each depth over many speckles. The resulting OCT profile is fitted to a mathematical expression to extract parameters.

In a tissue, the different layers can have a wide range of optical properties. When dispersing a single additive to scatter and absorb light in a polymer matrix, the signal profiles that can be mimicked are limited to pairs of backscattered amplitude and attenuation values of the additives available. Using a combination of additives that scatter and/or absorb light differently provides more liberty on the properties that can be obtained.

These additives can be fine particles in the form of powders added to a substantially transparent polymer matrix. Powders with particle dimensions on the order of the wavelength of light (to be used to examine and image the phantom) can be introduced in high enough concentration to provide a speckle field. Furthermore, by using powders, the concentration of scatterers in the phantom is directly known from the mass of powder put in a specific transparent matrix volume.

The choice of materials used to scatter and/or absorb light also has a certain impact on how the properties of the phantom evolve in time. To fabricate phantoms that keep the same properties over a long period, the preferred powders are inorganic, like metal oxides and inorganic pigments. Such powders are highly stable.

A preferred mixture is one that uses a first powder that mostly provides the backscattered amplitude, and a second powder that mostly provides attenuation. Our preferred choice of materials to match the response of various tissues to OCT systems working at a center wavelength of 1.3 µm is alumina and carbon black powders mixed in a transparent matrix. These powders do not degrade in time. When mixed in a stable matrix, they yield highly durable phantoms.

To determine the concentration of powders, knowledge of the relationships between the optical properties of the system and the concentration of components is required. For a powder in transparent matrix, the backscattered amplitude of OCT signal is proportional to the square root of the concentration of powder, and the total attenuation is directly proportional to the concentration. A more detailed description can be found our paper: Bisaillon et al, Physics in Medicine and Biology, 53 (13), (2008). When mixing different powders, the resulting backscattered amplitude measured by OCT ($A_{tot}$) is obtained by the quadratic addition of the amplitudes produced by the respective concentrations ($C_i$) of each powder (having backscattered amplitude ($A_i$), the backscattered amplitude being proportional to the square root of the concentration). The total attenuation ($\alpha_{tot}$) is obtained by the linear combination of the attenuation produced by each powder ($\alpha_i$) as a function of relative concentration. These relations are expressed by eq. 1 and eq. 2:

$$A_{tot} = \sqrt{\sum_i A_i^2} \text{ with } A_i \propto \sqrt{C_i}, \quad (eq.\ 1)$$

$$\alpha_{tot} = \sum_i \alpha(C_i). \quad (eq.\ 2)$$

OCT systems provide interference measurements on an arbitrary linear or logarithmic scale that maps the momentary intensity to the scale representing a dynamic range of signal intensities that can be measured. The relationship between the backscattered amplitude measured and the concentrations is system-dependent, varying by a constant of proportionality from one system to another. Therefore, to fabricate a phantom based on these relationships, the target values for the tissues must have been obtained with the same system. The system dependency is only required for the fabrication process. The relationship between the optical response of the resulting phantoms and the tissue is nevertheless system-independent. This means that the resulting phantom will mimic the tissue when measured with any OCT system operating in the same wavelength range.

The specific relationships between optical properties and concentration for certain compositions were obtained by producing sets of calibration samples and analyzing their signal profiles. A set of calibration samples can consist of cured mixtures that all have a different concentration of one single powder in the matrix.

Mixtures are prepared by weighing the needed amounts of alumina and carbon black, and then adding the necessary volume of the silicone resin. In some cases, the mixture viscosity was decreased with the addition of hexane in a volume that can be around half the volume of the resin. The alumina used in the present studies is a 1 µm de-agglomerated powder obtained from Struers (Mississauga, Canada). The carbon black is a product from Cabot (Boston, Mass.) called Monarch 700™, having a size distribution of about 40 to 100 nm. Both powders have small enough sizes to provide a speckle field. The silicone used was a mixture of pure poly (dimethyl siloxane) (Dow Corning 200R 50 cSt viscosity PDMS) and of Sylgard 184™ resin and reactive. The proportion of PDMS:Sylgard resin:Sylgard reactive was 15:15:1.

The mixture was sufficiently homogenized with at least 5 hours of sonication in an ultrasonic bath (Branson 1510), interrupted every hour by manual mixing. Afterwards, if needed, the hexane was evaporated in vacuum for a few hours. Finally the reactive is added and dispersed by manual mixing.

The mixture was then cured to form a layer by pouring the mixture into slab-shaped molds. The curing occurred at 70° C. in an oven during approximately one hour. The samples were imaged (B-scan) with a proprietary time domain OCT system as described in U.S. Pat. No. 7,428,086 performing 353 depth scans per second, with a depth resolution of about 15 µm and a transverse spot size of about 40 µm. The image is averaged in the transverse direction at each depth. The average depth profile is then fitted mathematically with an exponential decay that includes a correction for the incident beam and the collection of scattered light. This correction is obtained using a model according to Gaussian beam propagation theory. The fitting model has the form of eq. 3:

$$\frac{A}{\sqrt{1+(z/z_c)^2}} \exp[-2\alpha z], \quad (eq.\ 3)$$

where the fitted parameters A and α are the backscattered amplitude and the total attenuation, respectively. The variable z is the location in depth and $z_c$ is determined from the optical configuration of the OCT system.

Figure 3:
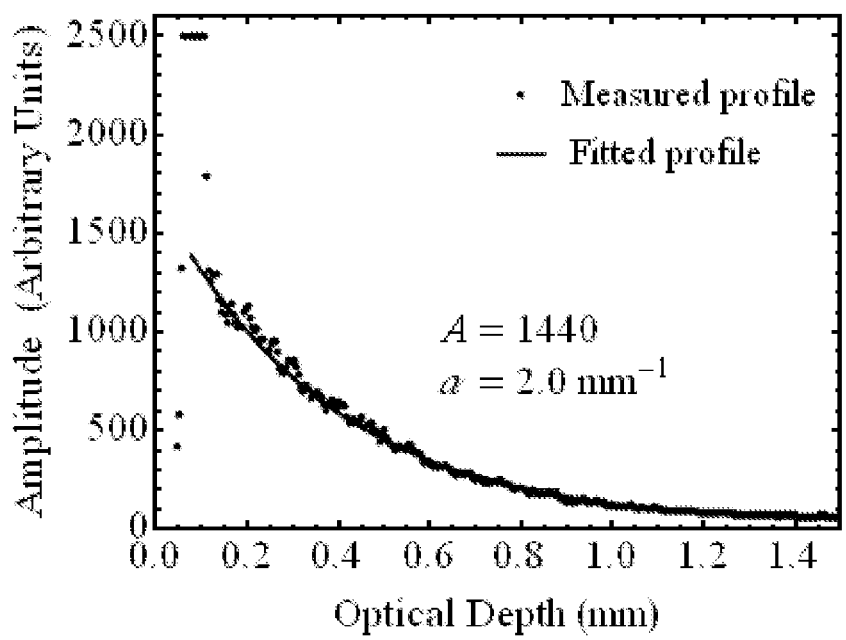
FIG. 3 is a graph of average backscattered amplitude as a function of depth for a calibration sample, and the curve resulting from its fit with a mathematical equation.

The analysis of the signal profile is illustrated in FIG. 3. It shows the average profile of a sample containing 20.5 mg/ml of alumina in the silicone matrix. The fitted exponential decay curve (according to the model) is also plotted over the data and the resulting fitting values (A=1440, α=2 mm$^{-1}$) obtained are also displayed.

After measuring all the samples from a set and after fitting their OCT profile, the needed relationships between concentration, and backscattering and attenuation coefficients, are obtained. FIGS. 4-7 show plots of backscattered amplitude or attenuation as a function of concentration for alumina and carbon black. The differences between these powders demonstrate clearly that the carbon black is a relatively good attenuator with less backscattering, whereas the alumina is a relatively good backscatterer with less attenuation. This permits various relative concentrations of these two components to span the range of attenuation and backscattering coefficients between these. Substantially alumina can be used to obtain a target level of the backscattering, and carbon black can be used to increase the attenuation with weak impact on the resulting backscattered amplitude.

Figure 4:
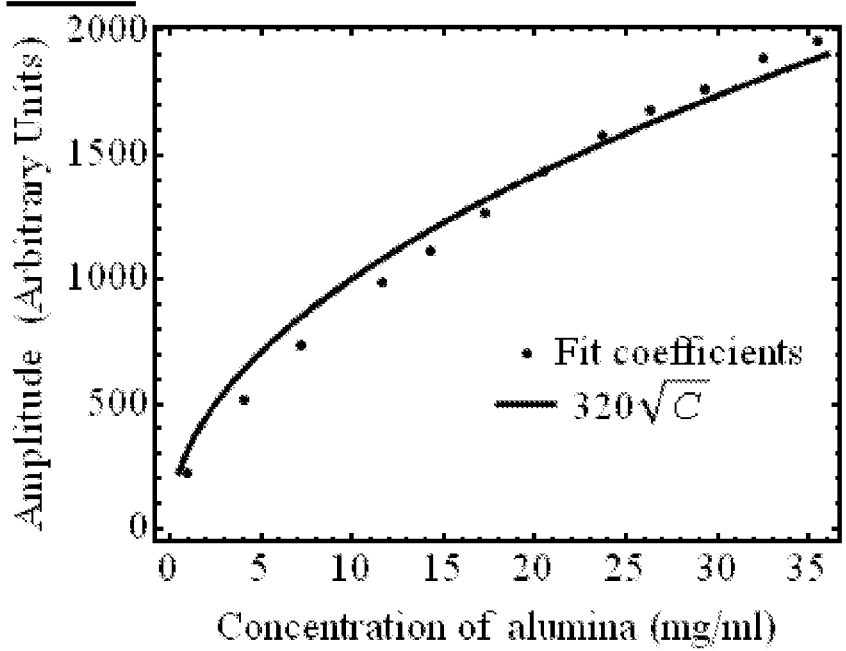
FIG. 4 is a graph of backscattered amplitude coefficients as a function of concentration for twelve (12) calibration samples of alumina powder in silicone.
Figure 5:
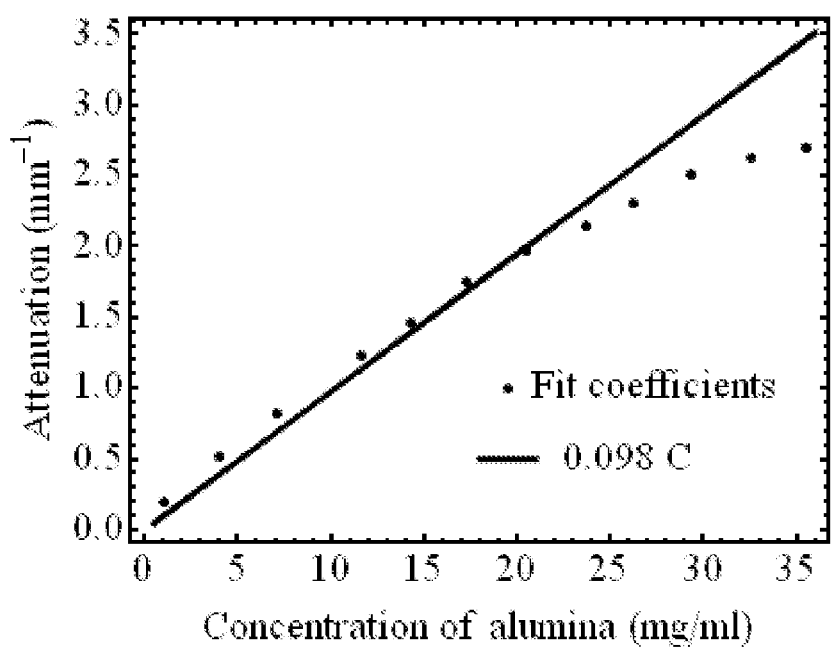
FIG. 5 is a graph of total attenuation coefficients as a function of concentration for twelve (12) calibration samples of alumina powder in silicone.
Figure 6:
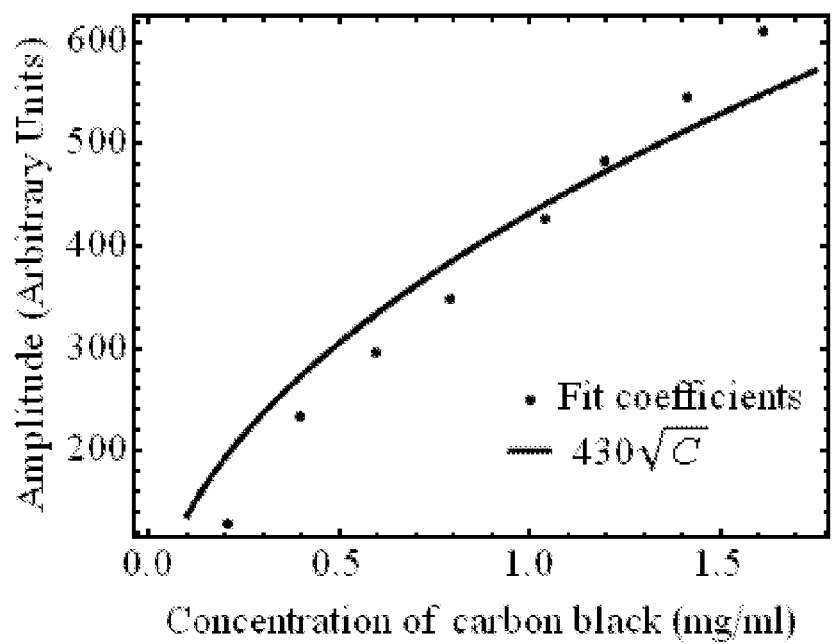
FIG. 6 is a graph of backscattered amplitude coefficients as a function of concentration for eight (8) calibration samples of carbon black powder in silicone.
Figure 7:
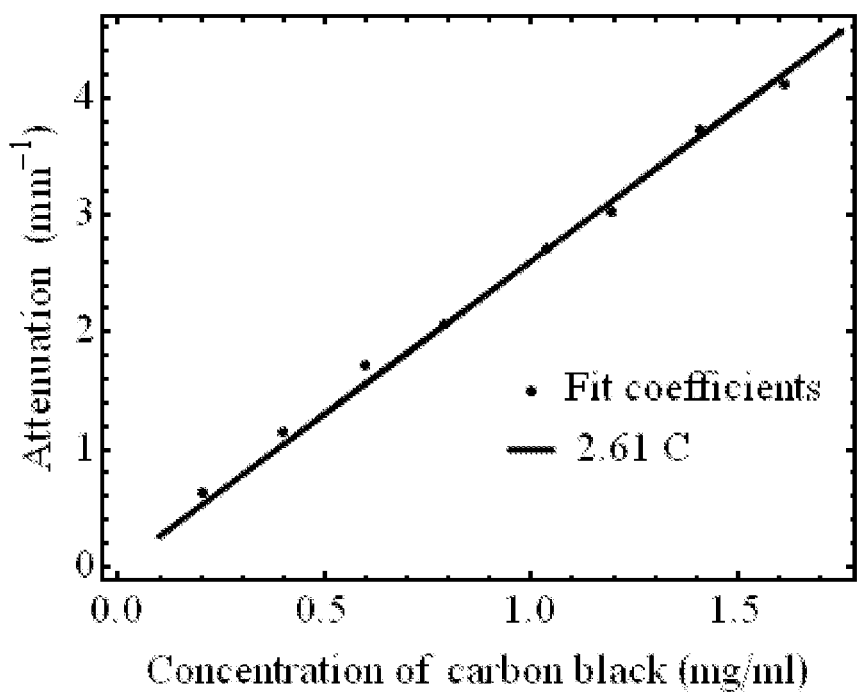
FIG. 7 is a graph of total attenuation coefficients as a function of concentration for eight (8) calibration samples of carbon black powder in silicone.

FIG. 4 shows a plot of the backscattered amplitude coefficients as a function of the concentration obtained from twelve samples of alumina in silicone. The relationship follows the expected square root dependency with a proportionality factor of about 320. Likewise, FIG. 5 shows the plot of the attenuation of the signal as a function of concentration. At low concentration, the linear dependency is respected, with a slope of about 0.098. FIG. 6 shows a plot of the backscattered amplitude coefficients as a function of the concentration obtained from eight samples of carbon black in silicone. The relationship somewhat follows the expected square root dependency with a proportionality factor of 430. FIG. 7 shows the plot of the attenuation of the signal as a function of the concentration. The linearity dependency is respected, with a slope of 2.61.

Mechanical Properties

Another aspect of our method for phantom fabrication is to obtain a resulting phantom that mechanically behaves, to a certain extent, like the target tissue. The mechanical behavior is the reaction to applied forces. Since a force can be applied in many different ways and strengths, the mechanical behavior can be described by a large number of properties. When fabricating a phantom for specific applications, one can specify how the forces are applied and choose to mimic specific mechanical properties of a tissue.

The method for fabricating multilayer phantoms is to form individual layers with respective amounts of powder additives in an elastomer matrix. The polymer matrix has the most impact on the mechanical properties. One very important property of tissues is their elasticity. This can be determined by measuring the force needed to stretch the material to a certain length. Materials that need smaller force to gain greater length have smaller elastic modulus. The variability of elastic modulus observed in tissues is accommodated by using different matrix materials.

The polymer matrix also has the most impact on the durability of the phantoms, and how it reacts to surrounding conditions. In the preferred embodiment, the layers are composed of different formulations of silicone. Each formulation provides a different elastic modulus. Additionally, using formulations based on the same silicone ensures that layers are well attached one to the other. Cured silicones are also highly stable. Phantoms of inorganic scatterers mixed in silicone have constant properties over many years. They also react with very few materials, and are especially stable in contact with materials that are compatible with a biomedical environment. Therefore, they are highly resistant in clinical conditions.

One specific silicone is Sylgard 184 which is sold as a kit composed of a resin and a reactive. The resin is a viscous liquid that allows the incorporation of powders. The addition of the reactive to the resin enables curing. Curing occurs within 48 hours at room temperature and within minutes at around 150° C. Curing temperature influences the elasticity of the resulting silicone. The elasticity is also influenced by the ratio of resin to reactive volumes used. The elasticity can be further adjusted by initially mixing poly(dimethyl siloxane) (PDMS) in the resin. Increasing the proportion of PDMS decreases the elastic modulus.

Figure 8:
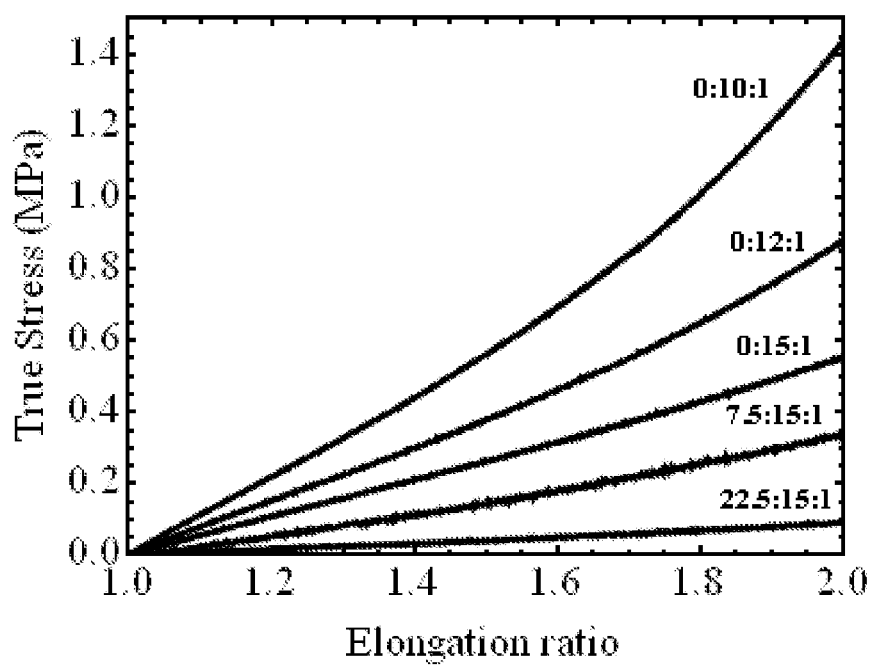
FIG. 8 is a graph of true stress as a function of elongation ratio of five (5) examples formed of PDMS, Sylgard 184 resin, and Sylgard 184 reactive in different proportions.

FIG. 8 shows the results of stretch tests performed on different formulations of silicone matrices. The true stress, defined as the stretch force divided by the area resulting from deformation, is plotted against the elongation ratio. The samples are made of Sylgard 184 resin and reactive, and Dow Corning 200R 50 cSt viscosity PDMS mixed in different ratios. Curves are identified on the right above with their ratios of PDMS:Sylgard resin:Sylgard reactive. A formulation for a specific phantom matrix can therefore be chosen to mimic the elasticity of the targeted tissue layer.

Additional Structures

The invention also includes methods to add volumetric structures to the phantoms. The volumetric structures can be located anywhere in the phantom, including on the inner and outer surfaces. In many cases, they represent pathologies like, for example, plaque in blood vessels. Their optical and mechanical properties are known and can differ from those of the layers.

To obtain a phantom with an embedded volumetric structure, after the formation of one or more layers by deposition and redistribution of the material, as described above the process is stopped. Prior to applying another layer, a solid feature is embedded at a location on the outer layer after the selective redistributing. This may be performed before the complete curing of the outer layer to assist in bonding of the solid feature to the outer layer. During the layer fabrication process, the layer material passes from viscous liquid to solid state. At some point in that process, the solidifying liquid is highly viscous, sticky in some cases, and has enough strength to somewhat maintain its shape and to support the incorporated solid material. At that point, the motions between the supporting and shaping elements may be stopped and the solid material is stuck on the phantom at the desired location.

In some cases, the location can be created by altering the previously deposited layer or layers, for example by cutting a hole to receive the material. Subsequently additional layers of the phantom are formed covering (or substantially covering) the solid feature. Positions between the supporting element and the shaping element may need to be adjusted relative to the solid material.

In some embodiments the solid feature has the desired properties of the phantom. In other embodiments, the solid feature is later removed either by fracturing the solid feature and removing the parts, or dissolving, melting or vaporizing the solid feature, for example by penetrating the additional layers to inject a fluid to dissolve the feature and suction to remove the solution, or by pumping to remove the liquefied or gasified solid object, for example. The removal of the solid feature may form a pocket within the phantom. This may be filled with a liquid, gas, or any fluid which may set, and provide desired mechanical and/or optical properties of a feature of the phantom. The penetration may leave a hole that may be subsequently repaired.

The solid features can be located on the outer and/or inner surfaces the multilayer phantom. The solid features may be put into place and then, a mixture of liquid polymer deposited locally and cured to embed the said material, at least partially, and to fix it to the phantom.

Example

Blood Vessel Embodiment

In one embodiment, the method we provide is used to produce blood vessel phantoms to be measured with OCT systems. Both types of blood vessels, arteries and veins, are tubular organs composed of three distinct tissue layers: the intima, the media, and the adventitia.

In this embodiment, the layer materials are mixtures of powders in silicone. In order to mimic the mechanical properties, the silicone is a mixture of Sylgard 184 and PDMS. The required OCT backscattered amplitude for each layer is mainly provided by alumina powder. The optical attenuation is adjusted with carbon black as required. With such compositions, the blood vessel phantoms are durable over many years and are highly resistant.

Figure 9:
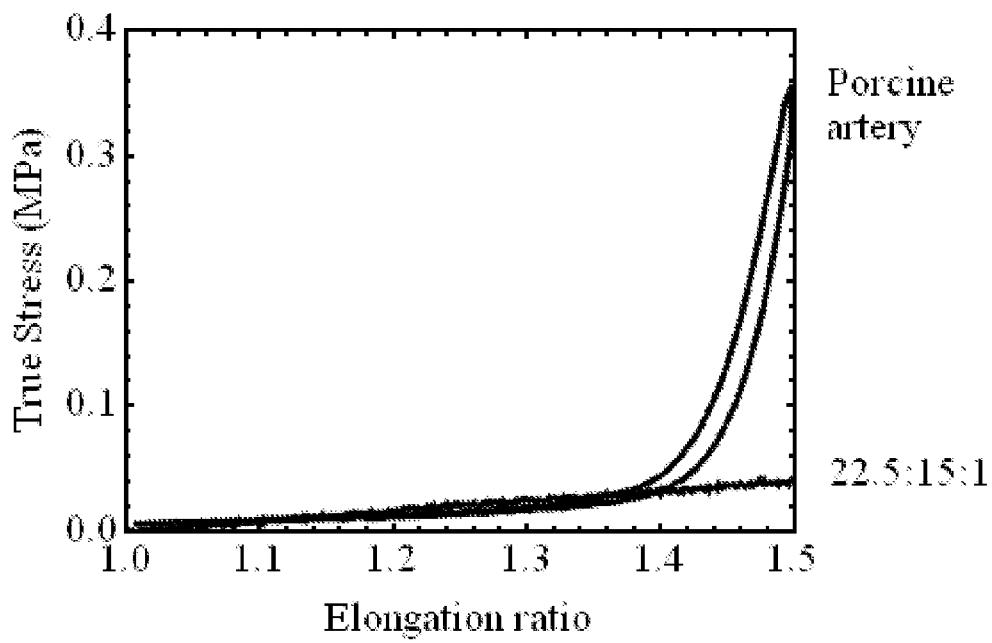
FIG. 9 is a graph comparing true stress as a function of elongation ratio for a sheet formed of 22.5:15:1 ratio of PDMS:Sylgard 184 resin:Sylgard 184 reactive, and for a porcine coronary artery.

The ratio of PDMS:Sylgard resin:Sylgard reactive to approximate the elasticity of the targeted tissue was determined experimentally. In this case, the mechanical behavior of a coronary artery is reproduced as a whole instead of for each layer separately. In FIG. 9, we show the result of traction tests performed on a porcine coronary artery and on a silicone material sample with a PDMS:Sylgard resin:Sylgard reactive ratio of 22.5:15:1. It shows that this particular formulation of silicone has an elastic modulus similar to that of the artery for small deformations, especially for up to 15% elongation where it is highly accurate. Up to 38% elongation (~25 kPa) the response of the porcine coronary artery and silicone material are similar. No effort was made to model at each layer the elastic modulus according to the present example.

Figure 10:
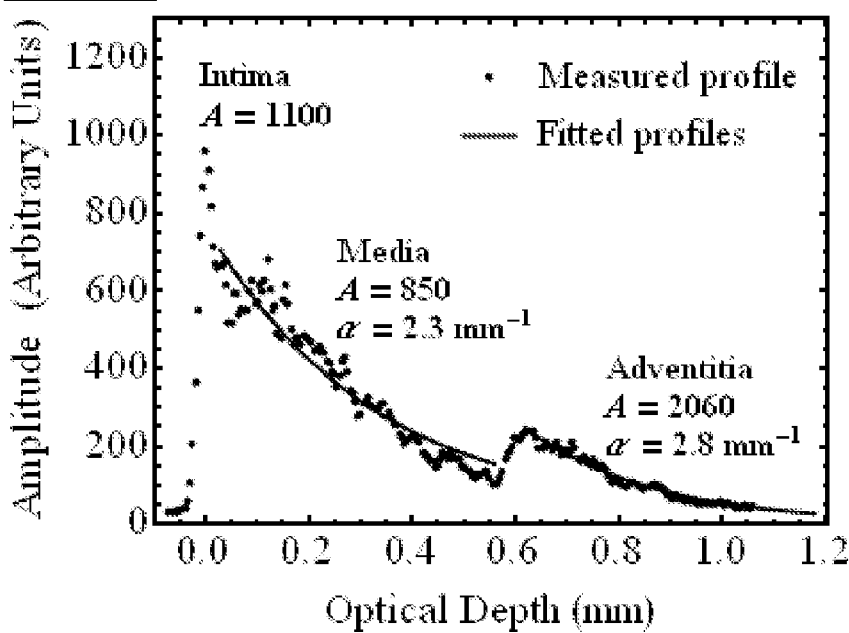
FIG. 10 is a graph of average backscattered amplitude as a function of depth for a porcine coronary artery and that of a curve resulting from the fit of the three tissue layers with a mathematical equation.

When measuring a porcine coronary artery with an OCT system, the three layers are clearly discernable as a result of different optical properties. Therefore, three mixtures with different concentrations in alumina and carbon black powders were used. To determine the required concentrations, the backscattered amplitude and total attenuation were obtained for each layer. The coronary artery was cut longitudinally, unfolded, and laid on a flat surface. It was imaged with the OCT apparatus in a benchtop configuration. For each layer the image is averaged at each depth. A profile is mathematically fitted for amplitude and total attenuation using eq. 3. A plot of the depth profile of a porcine coronary artery is presented in FIG. 10. The sections corresponding to each layer are discernable. The first section is very thin (about 10 μm) and corresponds to the intima. The second section (about 0.55 mm) corresponds to the media, and the third section, to the adventitia (about 0.45 mm). The fit curves are plotted over the amplitude and their corresponding values for the amplitude A and the total attenuation α are shown on the graph. No attenuation value is obtained for the intima because it is too thin.

The concentrations of alumina needed in each mixture to provide the respective backscattering values are obtained using the relationship between backscattered amplitude and concentration of alumina given in FIG. 4. This leads to concentrations of approximately 15 mg/ml for the intima, 10 mg/ml for the media, and 35 mg/ml for the adventitia. Using the relationship obtained in FIG. 5, we find that these concentrations produce total attenuations of $1.4\,\text{mm}^{-1}$, $0.9\,\text{mm}^{-1}$, and $2.7\,\text{mm}^{-1}$ respectively. For the media and the adventitia, the target attenuation coefficients are $2.3\,\text{mm}^{-1}$ and $2.8\,\text{mm}^{-1}$ respectively. For the adventitia, the target attenuation coefficient and the attenuation from alumina are sufficiently close. For the media, the attenuation needs to be increased by the addition of 0.5 mg/ml of carbon black powder. The required concentration of carbon black is obtained with FIG. 6.

An apparatus according to FIG. 1 was used to produce a phantom in accordance with an example of the invention. Three mixtures with the required powder concentrations were prepared and deposited and cured successively. The heating element provided a substantially uniform curing temperature of about 70° C. across the shaft throughout the layer forming. No hexane or other additive was used. The mixture ejected from the syringe as a rope which deformed slowly to spread across the surface. The blade wiped a majority of the material off, depending on a desired thickness of the layer.

A shaft with a 3 mm diameter was chosen and coupled to the rotation motor via the reducer. The distance between the blade and the shaft was adjusted to obtain the required layer thicknesses. The blade and the shaft were set to be parallel to obtain an even thickness all along the layers which had cylindrical inner and outer surfaces. The length of the blade used for shaping was 55 mm, and the length of the phantom was also 55 mm. Once the last layer has cured, the shaft was removed from the setup and the phantom was carefully detached from the shaft. The resulting coronary artery phantom was then ready for use.

The structure produced is essentially monolithic, as cross-section micrographs show that there is no boundary between the layers. This is desirable for the durability of the phantom, but may not be desired in all cases. If not desired, different compounds such as incompatible polymers can be used for different layers to reduce bonding, or complete curing with the application of coatings can be applied before a next layer.

The vessel produced had a very uniform distribution of thicknesses as was specifically desired in this instance. Control over the thickness to the degree produced was heretofore only obtained with molding, and molding of numerous layers requires many dies of respective qualities. The uniformity of the thicknesses of the 3 layers is advantageously controlled principally by mechanical devices (straightness of the blade, rectitude of the rotation, etc.) which can be produced for any desired measure of accuracy in a manner known in the art. Shrinkage rates (empirically or theoretically derived) may be used to predefine a thickness sought for a point on the layer to compensate for shrinkage.

The specific layers of the phantoms produced were not of thicknesses specifically chosen to emulate the porcine coronary artery, but rather were chosen to ensure visibility of the three layers with OCT characterization.

Figure 11:
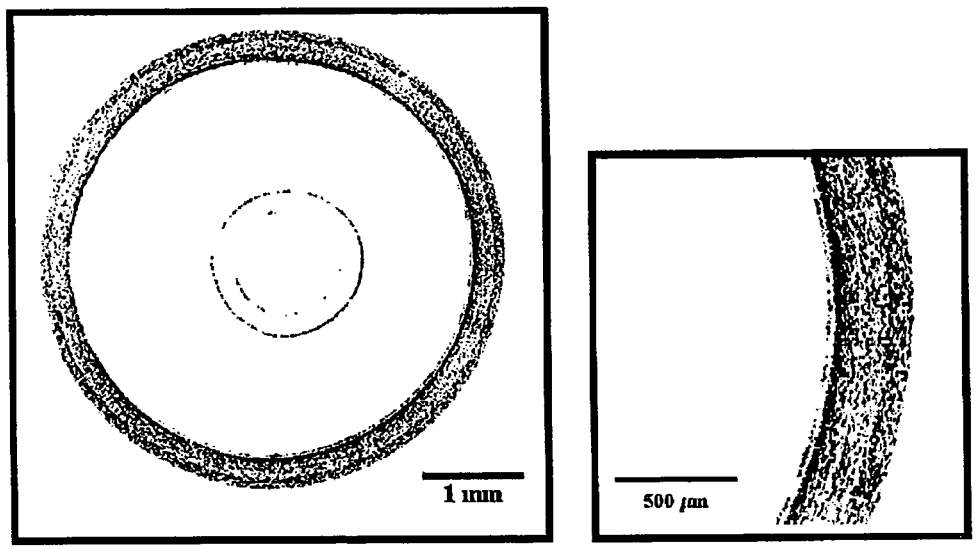
FIG. 11 is an OCT image showing the backscattered amplitude as a function of depth for a phantom produced as an example of the invention.

FIG. 11 is a schematic OCT image of the phantom produced according to the present example, and an enlarged view of a part thereof. The full image was taken in a mock surgery using an endoscopic probe head. The probe is encased in a protective guide catheter, encircled by a balloon. Inner and outer surfaces of the guide catheter are visible in a center of the complete image. The images of the phantom were taken with the balloon expanded.

These images show the intimal layer having a thickness of about 30 μm, a medial layer having a thickness of about 220 μm, and an adventitia of about 100 μm. All of the measures were within at least an estimated 10 μm uncertainty. This example is one of several produced using the present invention. A radial line of signal on the inner lumen is attributed to an inflated compliant balloon on which the phantom was supported for imaging. The enlarged image is grainy because of the angular step size between measurements.

Those of skill in the art will appreciate the similarity of the phantom as imaged with that of an artery, apart from the thicknesses of the layers being not drawn to scale.

The intimal layer of the phantom produced was not of a minimum thickness that can be provided using the apparatus shown. The thickness was made substantially thicker than in the porcine coronary artery to facilitate imaging of this layer. Applicant could reliably form layers of about 20 μm (~30 μm optical path length) or smaller using the present method.

Figure 12:
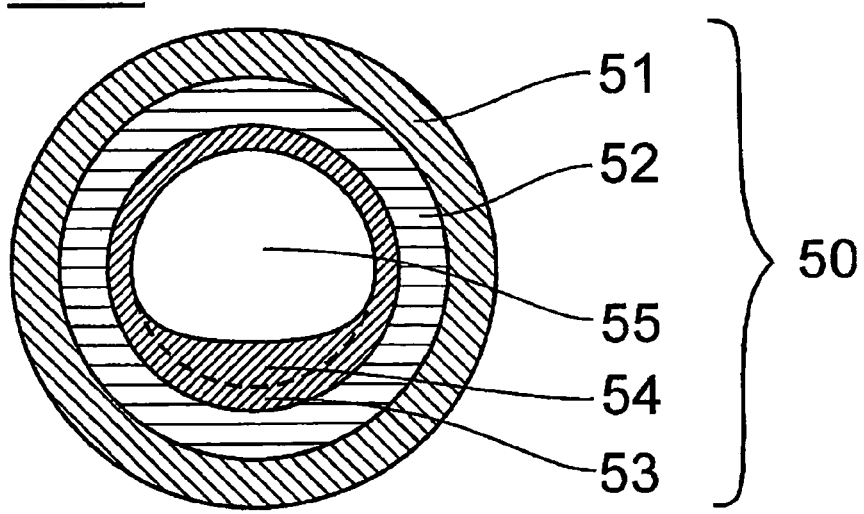
FIG. 12 is a schematic cross-sectional view of a coronary artery phantom with an added volumetric structure mimicking intimal thickening.
Figure 13:
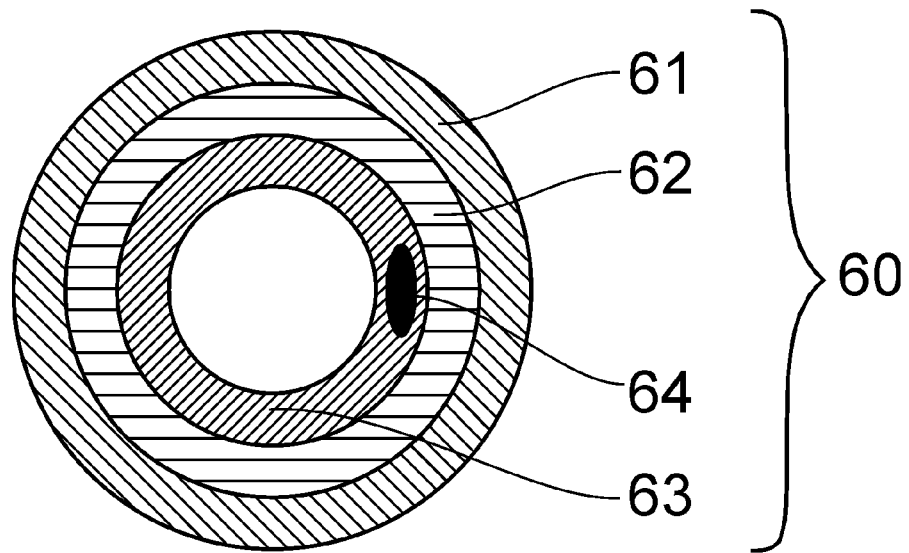
FIG. 13 is a schematic cross-sectional view of a coronary artery phantom with an added volumetric structure mimicking a calcification in a thickened intima.
Figure 14:
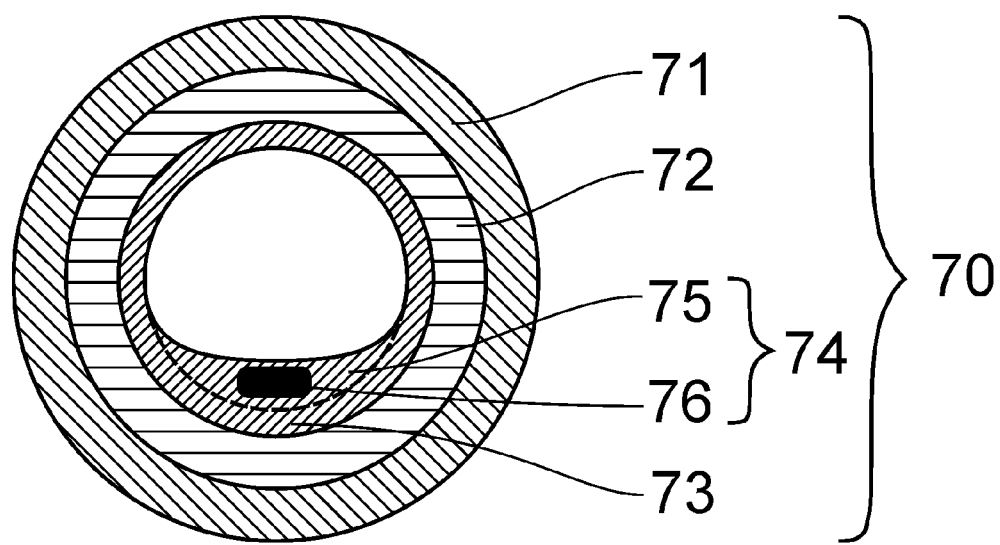
FIG. 14 is a schematic cross-sectional view of a coronary artery phantom with an added volumetric structure mimicking a lipid pool in a thickened intima.

In anticipated experiments, additional solid features will be added to the coronary artery phantoms to mimic diseases like, for example various features found in the different stages of atherosclerosis. FIGS. 12-14 schematically illustrate how these various features are expected to look, and below methods that are expected to be used to produce them according to the present knowledge.

FIG. 12 schematically illustrates a cross-section of a coronary artery phantom 50 with its three initial layers: the adventitia 51, the media 52, and the intima 53. An occlusion is provided at an axial location on the lumen by the deposition of liquid polymer, after the coronary artery phantom 50 is produced according to the above method. The alumina and silicone mixture used for the fabrication of the intima layer of the coronary artery phantom described above is deposited on the inner surface of the phantom with a syringe. The phantom with the non-covering material is then cured at a temperature of 150° C. in an oven to accelerate curing, and minimize the spreading. The deposition of the non-covering material, having the same properties as the intima 53 layer, narrows a lumen 55 of the phantom 50, mimicking intimal thickening, a pathological condition causing blood flow obstruction in a vessel.

FIG. 13 schematically illustrates a cross-section of another pathological coronary artery phantom 60 having an adventitia 61, media 62, and a thickened intima 63. A solid feature 64 is embedded in the intima 63. The process for forming the phantom is the same as before, except that the forming of the intima 63 is interrupted after only about half of the material was deposited and redistributed. As the first half of the intima 63 is curing, the forming is stopped. While the applied material is still sticky, a solid feature is applied to the surface. Fine particles can be sprinkled or large particles can be put in place at the desired location on the sticky outer surface. The solid feature may be formed of bone dust or calcium salt, which have high calcium concentrations and therefore mimic a calcification of a thickened intima. After the solid features were deposited, the rotation is restarted and the rest of the intima layer material is applied to cover the solid features. The phantom is completed by the fabrication of the media and the adventitia layers.

FIG. 14 schematically illustrates a cross-section of a third pathological coronary artery phantom 70 having an adventitia 71, media 72, and an intima 73 produced again by the above method. Phantom 70 has a solid feature 74 placed in the lumen of the phantom consisting of a solid material 76 shrouded by a non-covering material 75. The solid material 76 is put in place and removed to be replaced by a liquid material. The solid material can be a salt crystal. It is put at a desired location in the lumen of the artery phantom and is completely embedded 76 in the mixture used for the fabrication of the intima layer. The mixture is cured again at 150° C. to avoid spreading. After curing, the intima layer was perforated to create an access point. The phantom is then put in water overnight to completely dissolve the salt crystal. Then, the phantom is dried, and the void is filled with a liquid mixture of alumina and carbon black in silicone resin, without the reactive. Without the reactive, the mixture will not cure. The hole is then patched with the mixture mimicking the intima. Phantom 70 mimics a pathological condition where a lipid pool is embedded in a thickened intima.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

What is claimed is:

1. A method for producing a multilayer tissue phantom, the method comprising:
   successively forming at least two layers, each layer formed by:
      depositing a viscous flowable material to encircle at least a portion of a supporting element or over a previously formed layer of the phantom supported by the supporting element;
      selectively redistributing the material while the material is solidifying to control a thickness distribution of the layer; and
      allowing the material to solidify sufficiently to apply a next layer,
   wherein at least neighbouring layers are of different composition,
   wherein the compositions and thickness distributions of the layers are chosen to provide desired optical properties and mechanical properties of the phantom, and
   wherein selectively redistributing the material comprises contacting the material with a wiper while the wiper is in relative rotational motion with respect to the material.

2. The method of claim 1 further comprising successively forming a third layer.

3. A method for producing a multilayer tissue phantom, the method comprising:
   successively forming at least two layers, each layer formed by:
      depositing a viscous flowable material to encircle at least a portion of a supporting element or over a previously formed layer of the phantom supported by the supporting element;
      selectively redistributing the material while the material is solidifying to control a thickness distribution of the layer; and
      allowing the material to solidify sufficiently to apply a next layer,
   wherein at least neighbouring layers are of different composition,
   wherein the compositions and thickness distributions of the layers are chosen to provide desired optical properties and mechanical properties of the phantom, wherein selectively redistributing is performed by one of the following:
   by a wiper that extends a length of the phantom and bears a desired profile across that length whereby different thicknesses of the deposited layers may be deposited relative to the previously deposed layer, or the supporting surface;
   by a wiper, which extends a fraction of the length of the phantom, the wiper moving axially across the length of the phantom during the relative rotational motion, wherein radial motion of the wiper imparts a desired profile to the layer;
   in part by contacting the material with a wiper while rotating the supporting element along an axis wherein control over a radial position of the wiper is faster than the relative rotational motion and the layer has different thicknesses at different angles; or
   by a wiper which consists of a blade, an edge, a sharp point, or a rubber wiper.

4. The method of claim 1 wherein the viscous flowable material deposited comprises one of the following:
   a polymer resin selected for durability;
   at least 40 wt. % molten polymer resin;
   at least 40 wt. % curable polymer resin;
   at least 40 wt. % dissolved polymer in a volatile solvent;
   a silicone;
   a silicone with a poly(dimethyl siloxane);
   for each layer, a proportion of resin of silicone to poly (dimethyl siloxane) chosen to obtain a desired mechanical property for the layer;
   a same polymer resin in the composition of all layers;
   a selected amount of 0.0001-100 mg/ml of an optical attenuating additive;
   a selected amount of 0.0001-100 mg/ml of an optical scattering additive;
   an amount of an optical scattering and optical attenuating powder additives selected to provide:
      a backscattering amplitude for the layer proportional to a square root of a sum of the squared backscattering amplitudes of each of the powder additives for given concentrations; and
      an attenuation coefficient for the layer equal to a sum of attenuation coefficients of each of the powder additives for given concentrations;
   a selected amount of 0.0001-100 mg/ml of at least one of the following: carbon black, titania, and alumina, in powdered form:
   a selected amount of 0.0001-100 mg/ml of carbon black; or
   a selected amount of 0.0001-100 mg/ml of alumina.

5. The method of claim 1 wherein throughout the forming, the phantom is supported by the support element, which consists of a shaft, a rod, a tapered mandrel, or an inflated balloon, and is either (i) substantially covered by the phantom in 2 dimensions, (ii) substantially covered by the phantom in 3 dimensions, or (iii) has a profile corresponding to a cavity within an organ of an animal.

6. The method of claim 1 wherein depositing the viscous flowable material comprises one of the following steps:
   applying the material through a conduit that is translated axially over a length of the phantom said supporting element or the said previous layer;

applying the material through a conduit connected to the wiper;

applying the material through a conduit that is positioned with respect to an axis of the relative rotational motion that is at a substantially fixed angle with respect to the wiper;

applying the material at a part of a surface of the support element or the previously formed layer, and allowing a viscous flow under gravity to at least substantially coat the surface;

applying the material at a part of the surface that is rotating at a rate that is fast enough to prevent the material from dripping under the force of gravity, and slow enough to prevent ejection of the material by centrifugal force; or concurrently applying the material at one location while contacting previously deposited material at another location to selectively redistribute the material.

7. The method of claim 4 wherein allowing the material to solidify to a desired degree comprises controlling a temperature distribution of the layer and selecting a composition of the material that solidifies at a temperature higher than an ambient temperature.

8. The method of claim 1 wherein the step of forming one of the layers further comprises one of the following:

embedding a feature at a location on an outer layer after the selective redistributing;

embedding a solid feature at a location on an outer layer after the selective redistributing;

applying a compound at a location on an outer layer after the selective redistributing;

spraying a compound at a location on an outer layer after the selective redistributing;

embedding a solid feature at a location on an outer layer after the selective redistributing, and further comprising, after one or more subsequent layers are formed, penetrating the one or more subsequent layers to inject or remove material in contact with the solid feature;

embedding a solid feature at a location on an outer layer after the selective redistributing, and further comprising after one or more subsequent layers are formed, penetrating the one or more subsequent layers to inject a fluid to dissolve the solid feature, followed by removing the fluid and solute;

embedding a solid feature at a location on an outer layer after the selective redistributing, and further comprising after one or more subsequent layers are formed, penetrating the one or more subsequent layers to inject a fluid to dissolve the solid feature, followed by removing the fluid and solute and refilling a pocket formed within the phantom with another material;

embedding a solid feature at a location on an outer layer after the selective redistributing, and further comprising after one or more subsequent layers are formed, locally heating the solid feature until it exceeds a critical temperature, and penetrating the one or more subsequent layers to remove a fluidized part of the solid feature;

embedding a solid feature at a location on an outer layer after the selective redistributing, and further comprising after one or more subsequent layers are formed, locally heating the solid feature until it exceeds a critical temperature, penetrating the one or more subsequent layers to remove a fluidized part of the solid feature, and refilling a void created by the removal of the fluidized part with another material;

embedding a solid feature at a location on an outer layer after the selective redistributing, and further comprising after one or more subsequent layers are formed, locally heating the solid feature until it exceeds a critical temperature, penetrating the one or more subsequent layers to remove a fluidized part of the solid feature, refilling a void created by the removal of the fluidized part with another material, and repairing a hole in the phantom produced by the penetration;

embedding a solid feature at a location on an outer layer after the selective redistributing, and further comprising after one or more subsequent layers are formed, locally heating the solid feature until it exceeds a critical temperature, penetrating the one or more subsequent layers to remove a fluidized part of the solid feature, and refilling a pocket formed within the phantom with a fluid; or embedding a solid feature at a location on an outer layer after the selective redistributing, and further comprising after one or more subsequent layers are formed, locally heating the solid feature until it exceeds a critical temperature, penetrating the one or more subsequent layers to remove a fluidized part of the solid feature, refilling a pocket formed within the phantom with a fluid, and repairing a hole in the phantom produced by the penetration;

and further comprising one of the following steps:

applying a non-covering material in a liquid form on one of a part of an inner surface of an inner layer and a part of an outer surface of the outer layer and directing a flow of the non-covering material under the action of gravity to cover the part of the inner or outer surface without covering the whole of the inner or outer surface to solidify;

applying a non-covering material in a liquid form on one of a part of an inner surface of an inner layer and a part of an outer surface of the outer layer and directing a flow of the non-covering material under the action of gravity to cover the part of the inner or outer surface without covering the whole of the inner or outer surface to solidify, the non-covering material having a same composition as the inner layer or outer layer; or producing a hole in one of a part of an inner surface of an inner layer and a part of an outer surface of the outer layer and depositing a non-covering material in a liquid form in the hole, the non-covering material being of different composition than the inner or outer layer.

9. A method for using a phantom produced according to the method of claim 1, the method comprising inserting the phantom into an optical imaging system and imaging a portion of the phantom.

10. The method of claim 9 further comprising one of the following steps:

placing the phantom in contact with other tissue-like structures or liquids;

submitting the phantom to temperature variations or pressure variations that can be found normally or exceptionally in an animal;

testing a tool, process or implant on the phantom; or attaching a second phantom fabricated according to the method of claim 2 to the phantom such that lumens are coupled.

11. The method of claim 9 further comprising comparing independently characterized parameters of the phantom to calibrate the system.

12. The method of claim 9 further comprising inserting the phantom into a second optical imaging system, imaging the phantom using the second system, and comparing the image data from the system and second system to compare the two.

13. The method of claim 9 further comprising operating the system in a training mode to provide the user with feedback on the operation of the system.

\* \* \* \* \*